(12) United States Patent
Greenspan et al.

(10) Patent No.: US 6,663,878 B1
(45) Date of Patent: Dec. 16, 2003

(54) ANTI-INFLAMMATORY BIOACTIVE GLASS PARTICULATES

(75) Inventors: David C. Greenspan, Gainesville, FL (US); Sean Lee, Gainesville, FL (US); Marlo tan Walpole, Gainesville, FL (US)

(73) Assignee: USBIOMATERIALS Corp., Alachua, FL (US)

( * ) Notice: Subject to any disclaimer, the term of this patent is extended or adjusted under 35 U.S.C. 154(b) by 0 days.

(21) Appl. No.: 09/560,475

(22) Filed: Apr. 28, 2000

Related U.S. Application Data

(60) Provisional application No. 60/131,529, filed on Apr. 29, 1999.

(51) Int. Cl.[7] .............................. A61K 9/14; A61K 9/70; A61F 13/00; D02G 3/00; C12P 21/02
(52) U.S. Cl. ..................... 424/422; 424/443; 424/444; 424/85.1; 424/85.2; 424/489; 428/370; 435/69.5; 435/69.1; 435/69.51
(58) Field of Search ..................... 424/443, 449, 424/422, 85.1, 85.2; 435/69.5, 69.1, 69.51; 428/370

(56) References Cited

U.S. PATENT DOCUMENTS

| | | | |
|---|---|---|---|
| 4,103,002 A | 7/1978 | Hench et al. | |
| 4,272,518 A | 6/1981 | Moro et al. | |
| 4,303,066 A | 12/1981 | D'Andrea | |
| 4,538,603 A | 9/1985 | Pawelchak et al. | |
| 4,539,200 A | 9/1985 | Quarfoot | |
| 4,599,209 A | 7/1986 | Dautzenberg et al. | |
| 4,605,415 A | 8/1986 | Richez | |
| 4,613,502 A | 9/1986 | Turkova et al. | |
| 4,788,642 A | 11/1988 | Suzuki et al. | |
| 4,837,285 A | 6/1989 | Berg et al. | |
| 4,851,046 A | 7/1989 | Low et al. | |
| 5,000,746 A | 3/1991 | Meiss | |
| 5,017,627 A | 5/1991 | Bonfield et al. | |
| 5,068,122 A | 11/1991 | Kokubo et al. | |
| 5,126,141 A | 6/1992 | Henry | |
| 5,236,458 A | * | 8/1993 | Ducheyne et al. |
| 5,263,992 A | 11/1993 | Guire | |
| 5,290,544 A | 3/1994 | Shimono et al. | |
| 5,298,260 A | 3/1994 | Viegas et al. | |
| 5,340,776 A | 8/1994 | Paschke et al. | |

(List continued on next page.)

FOREIGN PATENT DOCUMENTS

| | | |
|---|---|---|
| WO | 97/17401 | 3/1994 |
| WO | 98/11853 | 3/1998 |
| WO | 99/13582 | 3/1999 |
| WO | 00/66086 | 11/2000 |

OTHER PUBLICATIONS

"Interaction of bioactive glasses with peritneal macrophages and minocytes in vitro", Bosetti et al, Journal of Biochemical Materials Research, 60 (1), pp. 79–85.*

(List continued on next page.)

*Primary Examiner*—Thurman K. Page
*Assistant Examiner*—Amy E Pulliam
(74) *Attorney, Agent, or Firm*—Burns, Doane, Swecker & Mathis, L.L.P.

(57) ABSTRACT

Compositions and methods for systemically minimizing the inflammatory effects of TNF-α are disclosed. The compositions include particles of bioactive glass with a particle size less than about 20 μm, alone or in combination with anti-inflammatory agents and other therapeutic agents. The compositions can include an appropriate carrier for oral, intramuscular, intraperitoneal or intravenous administration. When administered to a patient, the particles bring about elevated levels of IL-6 and do not cause elevated levels of TNF-α.

11 Claims, 8 Drawing Sheets

OTHER PUBLICATIONS

| | | | |
|---|---|---|---|
| 5,352,715 A | 10/1994 | Wallace et al. | |
| 5,410,016 A | 4/1995 | Hubbell et al. | |
| 5,501,706 A | 3/1996 | Arenberg | |
| 5,536,614 A | 7/1996 | Kondo et al. | |
| 5,591,453 A | 1/1997 | Ducheyne et al. | |
| 5,648,301 A | 7/1997 | Ducheyne et al. | |
| 5,681,575 A | 10/1997 | Burrell et al. | |
| 5,681,872 A | 10/1997 | Erbe | |
| 5,696,169 A | 12/1997 | Otsu et al. | |
| 5,707,829 A | * 1/1998 | Jacobs et al. | |
| 5,728,753 A | 3/1998 | Bonfield et al. | |
| 5,753,251 A | 5/1998 | Burrell et al. | |
| 5,766,611 A | 6/1998 | Shimono et al. | |
| 5,807,641 A | 9/1998 | Oku et al. | |
| 5,834,008 A | 11/1998 | Greenspan et al. | |
| 5,840,290 A | 11/1998 | Hench et al. | |
| 5,990,380 A | 11/1999 | Marotta et al. | |
| 6,083,521 A | 7/2000 | Acemoglu et al. | |
| 6,086,374 A | 7/2000 | Litkowski et al. | |

OTHER PUBLICATIONS

Aydin, M., et al., "Deposition Profile of Antibacterial Anodic Silver in Root Canal Systems of Teeth", *J. Biomed. Mater. Res.*, 38(1):49–54, (John Wiley & Sons, Inc.) 1997).

Barrett, E. P., et al., "The Determination of Pore Volume and Area Distributions in Porous Substances. I. Computations from Nitrogen Isotherms", *J. Am. Chem. Soc.*, 73:373–380 (American Chemical Society) 1951.

Bergna, H.E., "The Colloid Chemistry of Silica", *Advances in Chemistry*, Series 234 (American Chemical Society, Washington, DC) 1994.

Bosetti, M., et al., "Effects of Bioactive Glass on Macrophages Activation", *Bioceramics*, 11: 319–322, (Word Scientific Pub. Co.) 1998.

Brinker, C. J., et al., "The Physics and Chemistry of Sol–Gel Processing", *Sol–Gel Science*, 8: 499–503 (Academic Press, Inc.) 1990.

Brinker, C. J., et al., "The Physics and Chemistry of Sol–Gel Processing", *Sol–Gel Science*, 3: 115–119 (Academic Press, Inc.) 1990.

Carlisle, E. M., "Silicon Biochemistry, Silicon as an Essential Trace Element in Animal Nutrition", *Ciba Foundation Symposium 121*, 123–139 (John Wiley and Sons, New York) 1986.

Cartmell, S. H., et al., "Soft Tissue Response to Glycerol–suspended Controlled–release Glass Particulate", *J. Mat. Science: Mat. in Med.*, 9: 773–777 (Kluwer Academic Publishers) 1998.

Coleman, J. J., et al., "Mandibular Reconstruction with Composite Microvascular Tissue Transfer", *Medicine*, (Abstract) #91023289, 1991.

Freed, J. S., "Use of Injectable Biomaterials for the Repair and Augmentation of the Anal Sphincter", *Chemical Abstract*, 119:#195701, 1993.

Fung, M. C. et al., "Silver Products for Medical Indications: Risk–Benefit Assessment", *J. Toxicol.*, 34(1):119–126 (American Academy of Clinical Toxicology and European Association of Poisons Centres and Clinical Toxicologist) 1996.

Goldman Sachs/U.S. Research, "Advanced Tissue Sciences, (ATS)", (Healthcare: Biotechnology)1–30, 1996.

Greenspan, D. C., et al., "The Evaluation of Degradability of Melt and Sol–Gel Derived Bioglass® In Vitro", *Bioceramics*, 10:391–394 (Published by Elsevier Science) 1997.

Greenspan, D. C., et al., "Bioactivity and Biodegradability: Melt vs. Sol–Gel Derived Bioglass® In Vitro and In Vivo" *Bioceramics*, 11:345–348 (World Scientific Publishing Co.) 1998.

Grier, N., "Mercurials–Inorganic and Organic, Chapter 17" and "Silver and its Compounds, Chapter 18", *Disinfection, Sterilization and Preservation* (Lea & Febiger, $3^{rd}$ ed.) 1983.

Guo, et al., "Preparation and Studies of Bioactive Glass", *Chemical Abstracts*, v. 120: #144090, 1994.

Hench, L.. L.., , et al., *Biomaterials, An Interfacial Approach*, (Academic Press, New York) 1982.

Hench, L. L., et al., "The Sol–Gel Glass Transformation of Silica", *Phase Transitions, A Multinational Journal*, 24–26:785–834 (Gordon & Breach Science Publishers, S.A.)1990).

Hench, L. L. et al., "The Sol–Gel Process", *Chemical Reviews*, 90:33–72 (American Chemical Society) 1990.

Hench, L. L., et al., "Biological Applications of Bioactive Glasses", *Life Chem. Rep.*, 13:187–241 (Harwood Academic Publishers GmbH) 1996.

Hench, L. L., et al., "Introduction to Bioceramics, Chapter 1", *Advanced Series in Bioceramics*, 1: 1–24, (World Scientific) 1993.

Hench, L. L., et al., "Introduction to Bioceramics, Chapter 3", *Advanced Series in Bioceramics*, 3: 41–47, (World Scientific) 1993.

Hench, L. L., et al., "Introduction to Bioceramics, Chapter 4", *Advanced Series in Bioceramics*, 4: 63–79, (World Scientific) 1993.

Hench, L. L., et al., "Introduction to Bioceramics, Chapter 13", *Advanced Series in Bioceramics*, 13:239–259, (World Scientific) 1993.

Hench, L. L., et al., "Introduction to Bioceramics, Chapter 18", *Advanced Series in Bioceramics*, 18:319–334, (World Scientific) 1993.

Hench, L. L., et al., "Bonding Mechanisms at the Interface of Ceramic Prosthetic Materials", *J. Biomed. Mater. Res.*, 2: (1)117–141, (John Wiley & Sons, Inc.)1971 or 2?.

Hench, L. L., et al., "Bioactive Ceramics: Theory and Clinical Applications", *Bioceramics*, 7:3–14 (Butterworth–Heinemann Ltd.) 1994.

Jansen, B., et al., "In vitro Evaluation of the Antimicrobial Efficacy and Biocompatibility of a Silver–Coated Central Venous Catheter", *J. Biomater. Appl*, 9(1):55–70 (Technomic Publishing Co.) 1994.

Jansson, G., et al., "Stimulating Effects of Mercuric–and Silver Ions on the Superoxide Anion Production in Human Polymorphonuclear Leukocytes", *Free Rad. Res. Comms.*, 18(2):87–98 (Harwood Academic Publishers GmbH) 1993.

Kawashita, M., et al., "Preparation of Antibacterial Silver––Containing Silica Glass by Sol–Gel Method," *Bioceramics*, 11:703–706 (World Scientific Publishing Co.) 1998.

Keeting, P. E.,et al., "Zeolite A Increases Proliferation, Differentiation, and Transforming Growth Factor β Production in Normal Adult Human Osteoblast–Like Cells In Vitro", *J. Bone & Miner. Res.*, 7(11):1281–1289 (Mary Ann Liebert, Inc.) 1992.

Kelton, P. L., MD, "Skin Grafts", *Selected Readying in Plastic Surgery*, 7(2): 1–25, (Baylor University Medical Center) 1992.

Kim, T. N., et al., "Antimicrobial Effects of Metal Ions ($A^+$, $Cu^2$, $Zn^{2+}$) in hydroxyapatite", *J. Mater. Sci.–Mat. Med.*, 9:129–134 (Chapman & Hall) 1998.

Kokubo, T., et al., "Solutions Able to Reproduce in Vivo Surface–structure Changes in Bioactive Glass–Ceramic A–W$^3$", *J. Biomed. Mater. Res.*, 24:721–734 (John Wiley & Sons, Inc.) 1990.

Liau, S. Y., et al., "Interaction of Silver Nitrate with Readly Identifiable Groups: Relationship to the Antibacterial Action of Silver Ions", *Lett. Appl. Microb.*, 25:279–283 (Published for the Society for Applied Bacteriology by Blackwell Science) 1997.

Loeffler, U., et al., "Kit for in Situ Formation of Topical Gel for Enzyme Release in Wounds", *Chemical Abstracts*, 127:140–572, 1997.

Nogami, M. et al., "Glass Formation Through Hydrolysis of $Si(OC_2H_5)_4$ With $NH_4$ and HCI Solution", *J. Non–Chryst. Solids*. 37:191–201 (North–Holland Publishing Co) 1980.

Pereira, M. M., et al., "Effect of Texture on the Rate of Hydroxyapatite Formation on Gel–Silica Surface", *J. Am. Chem. Soc.*, 78(9):2463–2368, (Am. Ceramic Soc.) 1995.

Pereira, M. M., et al., "Homogeneity of Bioactive Sol–Gel Derived Glasses in the System $CaO-P_2O_5-SiO_2$", *J. Mater. Synth. Proces.*, 2(3):189–196 (Plenum Pub. Co. 1994.

Pereira, M. M., et al., "Mechanisms of Hydroxyapatite Formation on Porous Gel–Silica Substrates", *J. Sol–Gel Sci. Technol.*, 7:59–68 (Kluwer Academic Pub.)1996.

Pérez–Pariente, J., et al., "Influence of Composition and Surface Characteristics on the in Vitro Bioactivity of $SiO_2-CaO-P_2O_5MgO$", *J. Biomed. Mater. Res.*, 170–175, (John Wiley & Sons, Inc.) 1999.

Rabinovich, E. M., et al., "Fluorine in Silica Gels", *Bette Ceramics Through Chemistry II*, 251–259 (Brinker, Clark, Ulrich, eds, Materials Research Society, Pittsburgh, PA) 1986.

Reese, A. C., et al., "Role of Fibronectin in Wound Healing", *Current Advances in Oral and Maxillofacil Surgery*, 1: 1–25, (no date).

Scalzo, M., et al., "Antimicrobial Activity of Electrochemical Silver Ions in Nonionic Surfactant Solutions and in in Model Dispersions", *j. Pharm. Pharmacol.*, 48(1):60–63 (The Royal Pharmaceutical Society of Great Britain) 1996.

Shapiro, L., et al., "Ciliary Neurotrophic Factor Combined with Soluble Receptor Inhibits Synthesis of Proinflammatory Cytokines and Prostaglandin–$E_2$ in Vitro" *Exp. Cell. Res.,*, 215(1): 51–56, (Academic Press, Inc.) 1994.

Shirkanzadeh, M., et al., "Formation of Carbonate Apatite on Calcium Phosphate Coatings Containing Silver Ions," *J. Mat. Science, Mat. in Medicine*, 9:385–389 (Kluwer Academic Publishers) 1998.

Slawson, R. M., et al., "Geranium and Silver Resistance, Accumulation, and Toxicity in Microorganisms" *Plasmid*, 27(1): 72–79 (Bimonthly by Academic Press, Inc.)1992.

Stoor, P., et al., "Interactions Between the Frontal Sinusitis–Associated Pathogen *Haemophilus Influenza* and the Bioactive Glass S53P4", *Bioceramics*, 8:253–258 (Pergamon) 1995.

Stoor, P. et al., "Antibacterial Effects of a Bioactive Glass Paste on Oral Microorganisms", *Acta Odontol. Scand.*, 56:161–165 (Scandinavian University Press) 1998.

Theilmann, et al., "Two–Layer Bandage Made of a Polymer and a Water–absorbing Material", *Chemical Abstracts* 112:240557, 1990.

Ulich, T. R., et al., "Intratracheal Injection of LPS and Cytokines, V. LPS Induces Expression of LIF and LIF Inhibits Acute Inflammation", *Am. J. Physiol.*, 267 (4, pt. 1/2): L442–446 (The Am. Physiological Soc.) 1994.

Vrouwenvelder, C. A., et al., "Histological and Biochemical Evaluation of Osteoblasts Cultured on Bioactive Glass, Hydroxylapatite, Titanium Alloy, and Stainless Steel", *J. Biomed. Mater. Res.*, 27:465–475 (John Wiley & Sons, Inc.) 1993.

Warren, L. D., et al., "An Investigation of Bioglass Powders: Quality Assurance Test Procedure and Test Criteria", *J. Biomed Mater. Res.*, 23(A2):201–209 (John Wiley & Sons, Inc.) 1989.

Wells, T. N. C., et al, "Mechanism of Irreversible Inactivation of Phosphomannose Isomerases by Silver Ions and Flamazine", *Biochemistry*, 34(24):7896–7903 (American Chemical Society) 1995.

Wood, S, "Case Study: Traumatic Pressure Sore of the Left Lateral Malleolus", *Medicine*, (Abstract) 9315 543, 1993.

Wright, J. B., et al., "The Comparative Efficacy of Two Antimicrobial Barrier Dressings: In–vitro Examination of Two Controlled Release of Silver Dressings," *Wounds: A Compendium of clinical Research and Practice*, 10(6):179–188, (Westaim Biomedical Corp.)1998.

Zhong, J., et al., "Porous Sol–Gel Bioglass® From Near–Equilibrium Drying", *Bioceramics*, 10, 265–268 (Elsevier Science) 1997.

* cited by examiner

ANTI-INFLAMMATORY BIOACTIVE GLASS PARTICULATES

This application claims the benefit of Provisional Application Ser. No. 60/131,529 filed Apr. 29, 1999.

FIELD OF THE INVENTION

The present invention relates to compositions and methods for use in the transient suppression of the inflammatory response by suppressing plasma levels of tissue necrosis factor-alpha and increasing plasma levels of interleukin-6.

BACKGROUND OF THE INVENTION

When an injury occurs, cell damage initially comes from the precipitating event, such as a cut, resulting in ruptured cells and severed or crushed capillaries and other blood vessels. The interruption of blood flow results in anoxia, causing the death of additional cells. The wound site quickly fills with dead and dying cells, extracellular substances (collagen, elastic fibers, fat and ground substances), extravasated blood, and possibly bacteria and viruses introduced during the injury.

Tissue damage is not restricted to the initial area of injury, and may increase over the next several hours or days as a result of the release of lysomal enzymes from the injured cells or as a consequence of inflammation (swelling) and/or infection. (See Reese et al., Role of Fibronectin in Wound Healing, the subject matter of which is hereby incorporated by reference.) The inflammatory response is one of the normal stages of wound healing, and is necessary for subsequent phases of healing.

Inflammation is a vital process necessary for an organism to survive an external insult, such as a wound or burn. However, if unchecked, inflammation can have harmful consequences. For example, many chronic and even life-threatening disorders, such as asthma, rheumatoid arthritis, lung fibrosis, peritoneal adhesions, hypersensitivity and autoimmune diseases are a result of an uncontrolled inflammatory response. An unresolved inflammation in the lung resulting from bacterial infection (i.e., pneumonia) may eventually lead to extensive tissue damage and a chronic lung abscess. Inflammation of the peritoneal cavity, for example, and the resulting adhesions following abdominal surgery is a major cause of infertility in women. Asthma is an often life-threatening disorder which results from an inadvertently stimulated inflammatory response in the lungs. An excessive inflammatory response can cause extensive swelling, which can lead to additional injury as a result of anoxia. Pain results from a combination of kinins and the effect of lysozymes and pressure from the swelling on nerve endings. Unchecked, the inflammatory response can set off a neural feedback loop and cause hyperalgesia, a phenomenon in which the surrounding area of injury remains painful. Accordingly, there is a great interest in the medical community to develop anti-inflammatory agents.

Many known anti-inflammatory compositions reduce the inflammatory response, but are also immunosuppressive. For example, corticosteroids are potent anti-inflammatory agents, but are associated with T-cell suppression and increased infections. Interleukin-10 (as well as IL-4 and IL-3 to lesser extents) are broadly acting anti-inflammatory agents, but are associated with decreased cell mediated immune functions.

It would be advantageous to provide compositions and methods which provide protection from adverse effects associated with inflammation, preferably without unnecessary immunosuppression. The present invention provides such compositions and methods.

SUMMARY OF THE INVENTION

Compositions and methods for providing protection from adverse effects associated with inflammation are disclosed. The compositions and methods can suppress plasma concentrations of tissue necrosis factor-alpha (TNF-$\alpha$) while increasing plasma concentrations of interleukin-6 (IL-6).

The compositions include non-interlinked particles of bioactive glass with a size less than about 20 $\mu$m, alone or in combination with an additional anti-inflammatory agent, and optionally include other therapeutic agents. Formulations including the composition and a suitable carrier, preferably for oral, intramuscular, intraperitoneal or intravenous administration, are also disclosed.

The composition can be administered orally, intramuscularly, intraperitoneally or intraveneously to provide systemic relief from the adverse effects associated with inflammation, for example, the effects of excess TNF-$\alpha$.

DETAILED DESCRIPTION OF THE PREFERRED EMBODIMENTS

Figure 1:
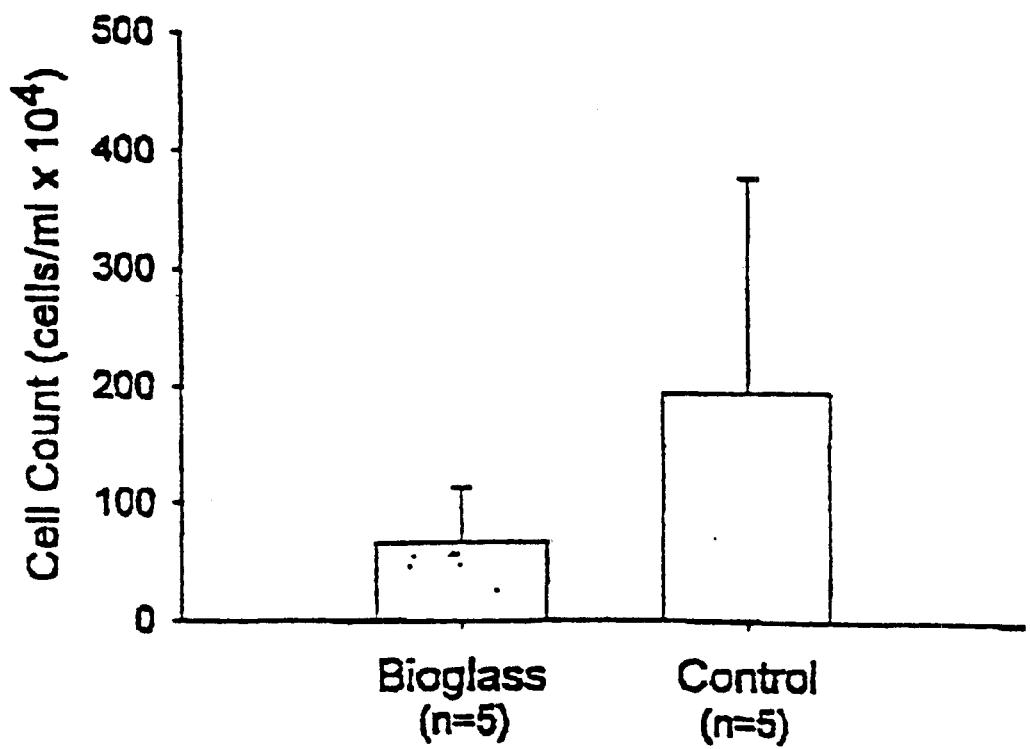
FIG. 1 is a graph showing the number of cells (cells/ml$\times 10^4$) for mice injected intraperitoneally with control and with bioactive glass, as described in Example 1.

Compositions and methods for providing protection from adverse effects associated with inflammation are disclosed. The compositions and methods can suppress plasma concentrations of tissue necrosis factor-alpha (TNF-$\alpha$) while increasing plasma concentrations of interleukin-6 (IL-6).

The compositions can be administered orally, intramuscularly, intraperitoneally or intraveneously to provide systemic relief from the adverse effects associated with inflammation, for example, the effects of excess TNF-$\alpha$. The bioactive glass is bioactive in vivo, and is not pro-inflammatory. It does not cause the recruitment of PMNs and does not stimulate TNF-$\alpha$ secretion. It stimulates IL-1$\beta$ release very modestly, and induces an IL-6 response.

IL-6 is a unique cytokine with pro- and anti-inflammatory properties. It is the primary hepatic acute phase response inducer (a pro-inflammatory effect). It suppresses TNF-α production by macrophages (an anti-iflammatory effect), promotes B-cell proliferation and promotes a $Th_2$ response, and is mitogenic for some cell types. It has been shown to reduce collagen induced arthritis (*Immunology*, 95(1):31 (1998)) and to reduce monocyte-mediated TNF production in response to LPS (*Exp. Cell Res.*, 215(1):51–56 (1994) and *Am. J. Physiol.* 267 (4pt.1):L442–446 (1994)).

The compositions include non-interlinked particles of bioactive glass with a size less than about 20 μm, alone or in combination with an additional anti-inflammatory agents, and optionally include other therapeutic agents. Formulations including the composition and a suitable carrier, preferably for oral or intravenous administration, are also disclosed.

The normal inflammatory effect is generally regarded as being ligand/receptor controlled. Not being bound to any particular theory or mechanism, it is believed that the rate and amount of ions generated by the absorption of the small particles of bioactive glass has an effect on the pro-inflammatory receptors, which is responsible for the suppression of the cytokines involved in the inflammatory process. Further, the surface of the small particles is microporous, and may adsorb the cytokines, rendering them inactive in the inflammatory process.

The compositions and methods described herein are advantageous because they reduce the inflammatory response, but are not broadly immunosuppressive. There does not appear to be a typical dose dependency in terms of particles of bioactive glass and IL-6 response. The response is independent of dose up to extremely high levels of particulate, for example, over XXX mg injection. Further, the bioactive glass particles appear to elicit a specific IL-6 response, transient in nature, lasting on the order of several hours. Pre-exposure to bioactive glass particles results in a significantly attenuated pro-inflammatory IL-6 cytokine response that results in the suppression of a typical inflammatory response caused by injection of an endotoxin after the injection of the bioactive glass particles.

The terms "wound" and "burn," collectively referred to herein as "injury" have their usual meanings. "Wound" is intended to include wounds caused by surgical procedures. "Normal" is used in the sense it is usually used in the medical arts. "Medical practitioner" means one of ordinary skill in the art wound and burn treatment. Typically, this person is a physician, nurse, dentist, or paramedic.

I. Bioactive Glass

Compositions including non-interlinked particles of bioactive glass with an average diameter of less than about 20 μm, alone or in combination with anti-inflammatory agents, can be used for the methods described herein.

Very small particulate bioactive glass has the property of exerting an anti-iflammatory effect when administered systemically. It appears that the bioactive glass suppresses the production of tissue necrosis factor alpha (TNF-α). TNF-α is a powerful pro-inflammatory cytokine that not only participates in the normal inflammatory response, but is also implicated in myocardial dysfunction and cardiomyocyte death in ischemia-reperfusion injury, sepsis, chronic heart failure, viral myocarditis and cardiac allograft rejection, as well as a host of other inflammatory disorders. Accordingly, by suppressing the production of TNF-α, the compositions reduce the likelihood of these disorders occurring.

The preferred size range for the bioactive glass, for this embodiment, is such that the particles do not physically obstruct vascular, lymph or pulmonary pathways as the particles pass through the body. As the particles are less than about 20 microns in size, they avoid phagocytosis and uptake by the reticuloendothelial system. This is in stark contrast to small particles of other materials, such as talcum, asbestos, silicone and metal debris, which are known to be strongly pro-inflammatory. The particles are of a suitable size for intravenous administration.

As used herein the terms "bioactive glass" or "biologically active glass" mean an inorganic glass material having an oxide of silicon as its major component and which is capable of bonding with growing tissue when reacted with physiological fluids.

Bioactive glasses are well known to those skilled in the art, and are disclosed, for example, in *An Introduction to Bioceramics*, L. Hench and J. Wilson, eds. World Scientific, New Jersey (1993), the contents of which are hereby incorporated by reference.

The glass preferably includes between 40 and 86% by weight of silicon dioxide oxide ($SiO_2$), between about 0 and 35% by weight of sodium oxide ($Na_2O$), between about 4 and 46% by weight calcium oxide (CaO), and between about 1 and 15% by weight phosphorus oxide ($P_2O5$). More preferably, the glass includes between 40 and 60% by weight of silicon dioxide oxide ($SiO_2$), between about 5–30% by weight of sodium oxide ($Na_2O$), between about 10 and 35% by weight calcium oxide (CaO), and between about 1 and 12% by weight phosphorus oxide ($P_2O5$). The oxides can be present as solid solutions or mixed oxides, or as mixtures of oxides. $CaF_2$, $B_2O_3$, $Al_2O_3$, MgO and $K_2O$ may be included in the composition in addition to silicon, sodium, phosphorus and calcium oxides. The preferred range for $B_2O_3$ is between 0 and 10% by weight. The preferred range for $K_2O$ is between 0 and 8% by weight. The preferred range for MgO is between 0 and 5% by weight.

The most preferred glass is Bioglass®™ (a trademark of University of Florida), which has a composition including about 45% by weight silicon dioxide, about 24.5% by weight sodium oxide, about 6% by weight phosphorus oxide, and about 24.5% by weight calcium oxide. Another preferred material is hydroxyapatite.

Particulate, non-interlinked bioactive glass is preferred in the present invention. That is, the glass is in the form of small, discrete particles, rather than a fused matrix of particles or a mesh or fabric (woven or non-woven) of glass fibers. Note that under some conditions the discrete particles of the present invention may tend to cling together because of electrostatic or other forces but are still considered to be non-interlinked. The particle size is less than about 20 microns, preferably 10 microns or less, more preferably less than about 5 microns, and ideally, less than about 2 microns.

The glass composition can be prepared in several ways, to provide melt-derived glass, spun fibers of sol-gel derived glass, and sintered glass particles. The sintered particles may be in sol-gel derived, or pre-reacted melt derived form. Sol-gel derived glass is generally prepared by synthesizing an inorganic network by mixing metal alkoxides in solution, followed by hydrolysis, gelation, and low temperature (600–900° C.) firing to produce a glass. Melt derived glass is generally prepared by mixing grains of oxides or carbonates, melting and homogenizing the mixtures at high temperatures, typically between about 1250 and 1400° C. The molten glass can be fritted and milled to produce a powder or casted into steel or graphite molds to make bulk implants.

The glass composition is preferably melt-derived. In each preparation, it is preferred to use reagent grade glass, especially since the glass is used to prepare materials which ultimately may be implanted in a human. Other compositions which biodegrade and release the same ions as the bioactive glasses described above can also be used, provided they do not elicit an inflammatory response and that they also elicit enhanced IL-6 production.

A. Melt Derived Glass

A melt-derived glass composition can be prepared, for example, by preparing an admixture of the individual metal oxides and other components used to prepare the glass composition, blending the admixture, melting the admixture, and cooling the mixture. The melting temperature is determined in large part by the glass composition, and ranges, for example, from about 900–1500° C., preferably between about 1250 and 1450° C. The melt is preferably mixed, for example, by oxygen bubbling, to ensure a thorough homogenation of the individual components.

The mixture can be cooled, for example, by adding the molten admixture to a suitable liquid, such as deionized water, to produce a glass frit. Porosity can be introduced by grinding the glass into a powder, admixing the powder with a foaming agent, and hot pressing the mixture under vacuum and elevated temperature. The particle size of the glass powder is between about 40 and 70 $\mu$m, the vacuum is preferably less than 50 MPa, and the hot pressing is preferably performed at a temperature above 400° C., preferably between about 400 and 500° C. Suitable foaming agents include compounds which evolve carbon dioxide and/or water at elevated temperatures, for example, metal hydroxides, metal carbonates, and peroxides, such as hydrogen peroxide. Preferred metal carbonates are sodium bicarbonate, sodium carbonate and calcium carbonate. The foaming agents are preferably added in a range of between about 1–5, more preferably 2–3 percent by weight of the glass powder. The preparation of melt-derived porous glass is described, for example, in U.S. Pat. No. 5,648,301 to Ducheyne and El Ghannam, the contents of which are hereby incorporated by reference.

B. Sintered Glass Particles

Glass can be sintered using known methodology. In one embodiment, an aqueous slurry of the glass powder and a foaming agent with a suitable binder, such as polyvinyl alcohol, is formed. The slurry is then poured into a mold, allowed to dry, and sintered at high temperatures. These temperature may range, depending on the glass composition and foaming agent used, between about 500 and 1000° C., more preferably between about 600 and 800° C.

C. Spun Fibers of Sol-gel Derived Glass

It is known in the art to control the heat treatment cycle of glass gels to control the pores and interpores of the material to create a porous glass material. Suitable pore diameters are between 20 and 180 Å, suitable pore volumes are between 40 and 52 cc/g, and suitable surface areas are between 75 and 350 m$^2$/g. Since a pore diameter larger than 0.1 microns is difficult to achieve using this method, the sintering and foaming processes described herein are generally more preferred.

D. Leaching of the Porous Material

To aid in preparing glass compositions with high porosity, the glass composition can include a material which can be preferably leached out of the glass composition, and, in doing so, provide the composition with high porosity. For example, minute particles of a material capable of being dissolved in a suitable solvent, acid, or base can be mixed with or melted into the glass, and subsequently leached out. The resulting voids have roughly the same size as the particle that was leached out. In the case of a material which is part of a melt-derived glass composition, the size of the pores and degree of porosity depends on the amount of added material relative to the amount of glass. For example, if the leached material constituted about 80% of the glass, then the glass would be approximately 80% porous when the material was leached out. When leaching the glass composition, care should be taken not to leach out those components which add to the bioactivity of the glass, i.e., the calcium and phosphorus oxides.

II. Formulations Including Bioactive Glass

The bioactive glass particulates are preferably administered in a formulation that includes an acceptable carrier for the mode of administration. Suitable pharmaceutically acceptable carriers are known to those of skill in the art. The formulations can optionally include other therapeutically active ingredients, such as antibiotics, antivirals, healing promotion agents, anti-inflammatory agents, immunosuppressants, growth factors, anti-metabolites, cell adhesion molecules (CAMs), antibodies, vascularizing agents, anti-coagulants, and anesthetics/analgesics.

The carrier must be pharmaceutically acceptable in the sense of being compatible with the other ingredients of the formulation and not deleterious to the recipient thereof. The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include a sterile aqueous preparation of the bioactive glass. Such formulations may conveniently contain distilled water, 5% dextrose in distilled water or saline. The formulations may be in the form of a powdered formulation including the bioactive glass particulates and salt, dextrose, buffers and the like, which can be dissolved in water immediately prior to administration.

For enteral administration, the bioactive glass particulates can be incorporated into an inert carrier in discrete units such as capsules, cachets, tablets or lozenges, each containing a predetermined amount of the particles; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Other Therapeutic Agents

In addition to bioactive glass particles, the formulations can include other therapeutic agents such as antibiotics, antivirals, healing promotion agents, anti-inflammatory agents, immunosuppressants, growth factors, antimetabolites, cell adhesion molecules (CAMs), bone morphogenic proteins (BMPs), vascularizing agents, anticoagulants, and topical anesthetics/analgesics.

The antibiotics can be topical antibiotics suitable for skin treatment. Examples of such antibiotics include but are not limited to: chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline and chlortetracycline.

Suitable antivirals include topical antivirals, such as acyclovir and gancyclovir. Suitable anti-inflammatory agents include corticosteroids, hydrocortisone and nonsteroidal anti-inflammatory drugs. Suitable growth factors include basic fibroblast growth factor (bFGF), epithelial growth factor (EGF), transforming growth factors $\alpha$ and $\beta$ (TGF $\alpha$ and $\beta$), platelet-derived growth factor (PDGF), and vascular endothelial growth factor/vascular permeability factor (VEGF/VPF)). Suitable topical anesthetics include benzocaine and lidocaine.

An additional anti-inflammatory agent which can be used in combination with the bioactive glass particles is $\beta$-glucan. $\beta$-glucan is a polysaccharide with anti-inflammatory properties, and, like the bioactive glass particles described herein, increases IL-6 release and decreases TNF-$\alpha$ and IFN$\gamma$ release.

III. Methods of Reducing Inflammation

The compositions can be used to prophylactically or therapeutically to reduce inflammation in a patient. Overly acute or chronic inflammation can result in various disease states in a patient, for example, arthritis and tendonitis, pulmonary disorders such as asthma and emphysema, and postsurgical (peritoneal) adhesions.

The particles of bioactive glass are believed to modify the inflammatory response in the local microenvironment by altering the synthetic properties of resident macrophages and other recruited inflammatory cells. The particles induce macrophage tolerance by eliciting a cytokine response (IL-6 based) that acts in an autocrine and paracrine fashion.

Particles of bioactive glass can be delivered by intravenous, intramuscular, or intraperitoneal injection to provide systemic (and possibly local when administered intramuscularly or intraperitoneally) anti-inflammatory effects. These effects can be therapeutic and/or prophylactic. For example, systemic delivery of bioactive glass can be effective in reducing the onset of inflammation brought on by external challenge. Particles of bioactive glass can also be administered orally.

Systemic administration of the bioactive glass particles can lower production of TNF-$\alpha$ and also increase production of IL-6. The effect of this is to modify the pro-inflammatory response, and will be useful in treating or preventing sepsis, systemic inflammatory response syndromes, adult respiratory distress syndrome, ocular injury, surgical wound healing and adhesion formation, and delayed cutaneous wound healing. Other disorders which are, at least in part, attributable to an exaggerated inflammatory response, such as ARDS, pancreatitis, viral hepatitis, hemorrhagic shock, ischemia/reperfusion injury, peritoneal adhesions, and chronic inflammation, such as delayed wound healing and rheumatoid arthritis, can be treated with systemic administration of bioactive glass particles.

In one embodiment, the particles are administered locally, for example, by inhalation, by spraying (in the form of an aerosol) or by mixing the particles with a gel (for example, a biocompatible hydrogel), creme or other aqueous or nonaqueous carrier, and applying or injecting the composition subcutaneously at a site at which surgery is to be performed at a later time. The compositions can advantageously include an anesthetic. The presence of the particles at the proposed surgical site can lead to decreased inflammation resulting from the surgery.

The present invention will be more clearly understood with reference to the following non-limiting examples.

EXAMPLES

Example 1

Intraperitoneal Administration of Bioactive Glass to Mice

Ten mice were injected intraperitoneally with 25 mgs of bioactive glass (45S5) with a particle size less than about 20 $\mu$m in a total volume of 1 ml (0.5 ml fetal calf serum and 0.5 ml phosphate-buffered saline) with a result pH of 9.6. An additional ten mice received the carrier (0.5 ml fetal calf serum and 0.5 ml phosphate-buffered saline) with the pH unadjusted. Two hours later, the mice were euthanized and the peritoneal contents were washed with 3 ml of physiologic saline. Peritoneal white cell count was performned with a hemocytometer, and peritoneal TNF-$\alpha$ and IL-6 determined by ELISA.

Figure 2:
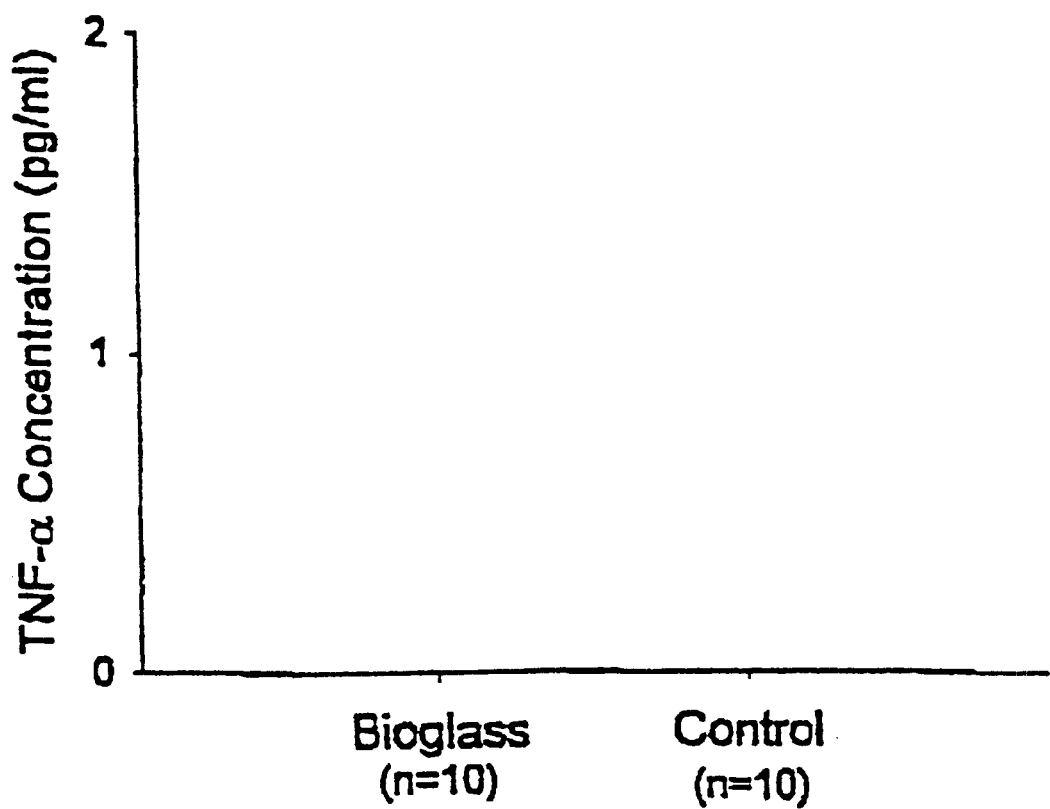
FIG. 2 is a graph showing the concentration of TNF-$\alpha$ (pg/ml) for mice injected intraperitoneally with control and with bioactive glass, as described in Example 1.
Figure 3:
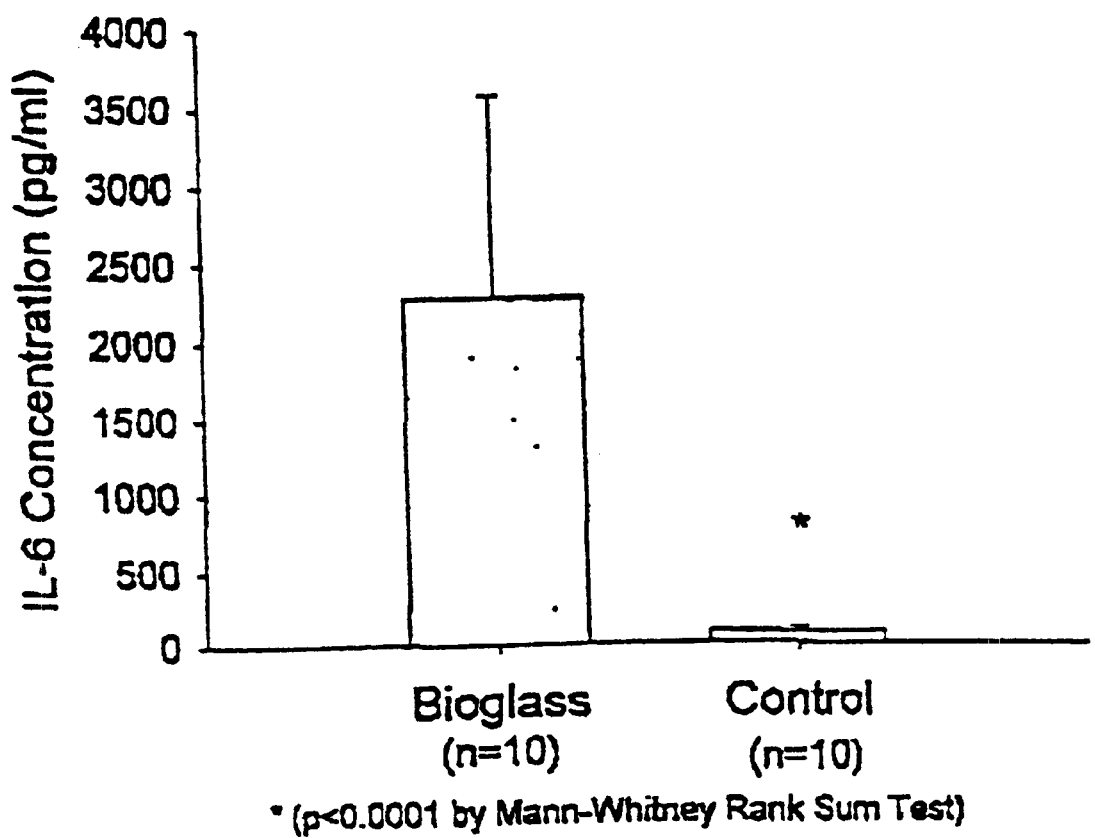
FIG. 3 is a graph showing the concentration of IL-6 (pg/ml) for mice injected intraperitoneally with control and with bioactive glass, as described in Example 1.

The procedures were performned without incident. The animals appeared grossly normal for the two hour post-injection period. At sacrifice, peritoneal white cell count in mice receiving the bioactive glass particles was not different from peritoneal wash fluid from ice receiving only the carrier. The proinflammatory cytokine TNF-$\alpha$ was not detected in any of the samples. Peritoneal IL-6 concentrations, however, were increased 25 fold from approximately 80 pgs/ml in the carrier-treated mice to over 2,000 pgs/ml in the bioactive glass-treated mice. The cell count, TNF-$\alpha$ concentration and IL-6 concentration from the peritoneal washings for the bioactive glass-treated mice and the control mice are shown in FIGS. 1–3.

In conclusion, the bioactive glass is bioactive when administered intraperitoneally. The bioactive glass is not acting as a classical irritant. A chemical irritation or a direct inflammatory agent like endotoxin or TNF-$\alpha$ would have resulted in a significant and rapid neutrophil influx, which was not observed. The bioactive glass was not directly pro-inflammatory, since no TNF-$\alpha$ response was elicited. A significant IL-6 response was observed, but IL-6 has both pro-inflammatory (hepatic acute phase induction) and anti-inflammatory properties (delays apoptosis, suppresses macrophase TNF and IL-1 production). Since no inflammatory cell influx was observed, the enhanced IL-6 production must have been secondary to resident macrophages and fibroblasts. The results are consistent with bioactive glass-mediated stimulation of resident cell IL-6 synthesis, which represents a new anti-inflammatory property.

Example 2

Anti-Inflammatory Effect of Bioactive Glass in a Mouse Endotoxicosis Model

Figure 4:
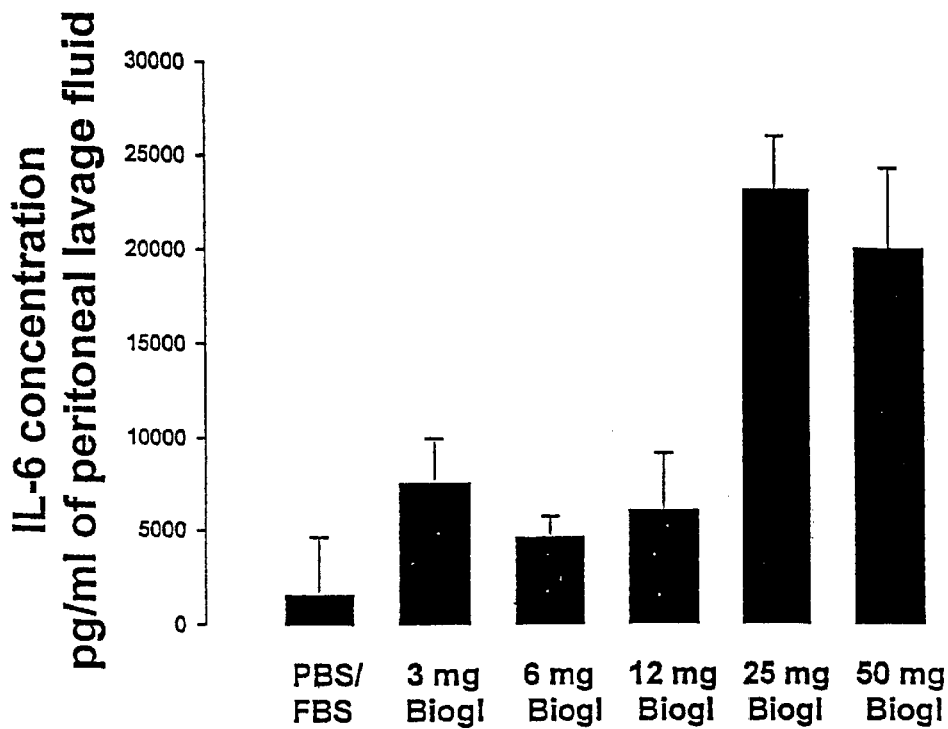
FIG. 4 is a graph showing the concentration of IL-6 (pg/ml) for mice injected intraperitoneally with varying doses of bioactive glass, as described in Example 2.

Bioactive glass particles with a particle size of 5 $\mu$m were injected to C57B1/6 mice. The mice were injected ip with 3, 6, 12, 25 and 50 mg of bioactive glass particles or buffer. The animals were sacrificed and TNF-α, IL-1α and IL-6 levels were determined in the peritoneal lavage fluid at 2 hours (FIG. 4). In a second study, mice were injected with 12 mg of bioactive glass particles or buffer ip and then challenged ip with 1 μg of LPS and 8 mg of D-galactosamine (Dgal) 6 hours after the bioactive glass particles were administered. Blood samples were taken 90 minutes after Dgal/LPS injection for determination of TNF-α. Lastly, a sublethal dose of LPS (100 ng) was given ip 2 hours after an ip injection of 3 mg of 5 μm particles of bioactive glass. The mice were bled, sacrificed and ravaged 2 hours after the LPS administration.

Figure 5:
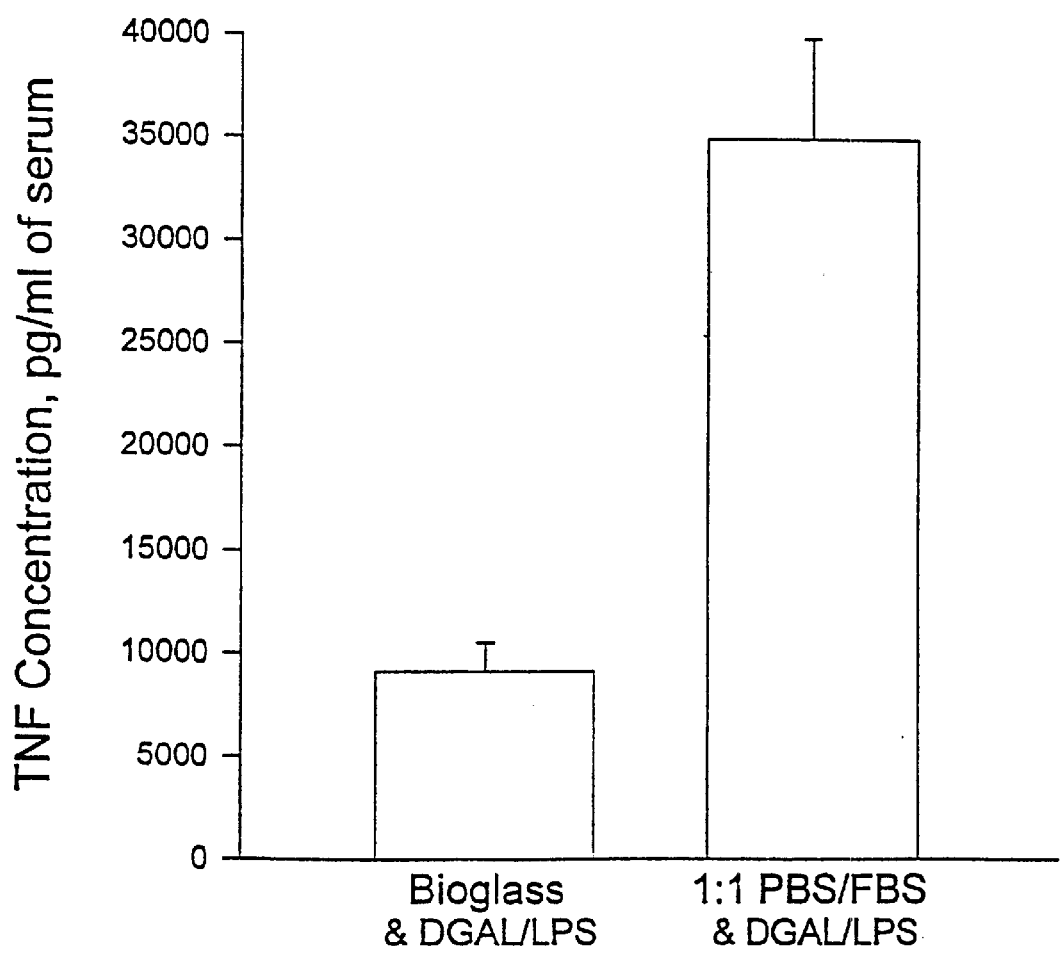
FIG. 5 is a graph showing the concentration of TNF-$\alpha$ (pg/ml) for mice injected intraperitoneally with bioactive glass and LPS/D-galactosamine, as described in Example 2.
Figure 6:
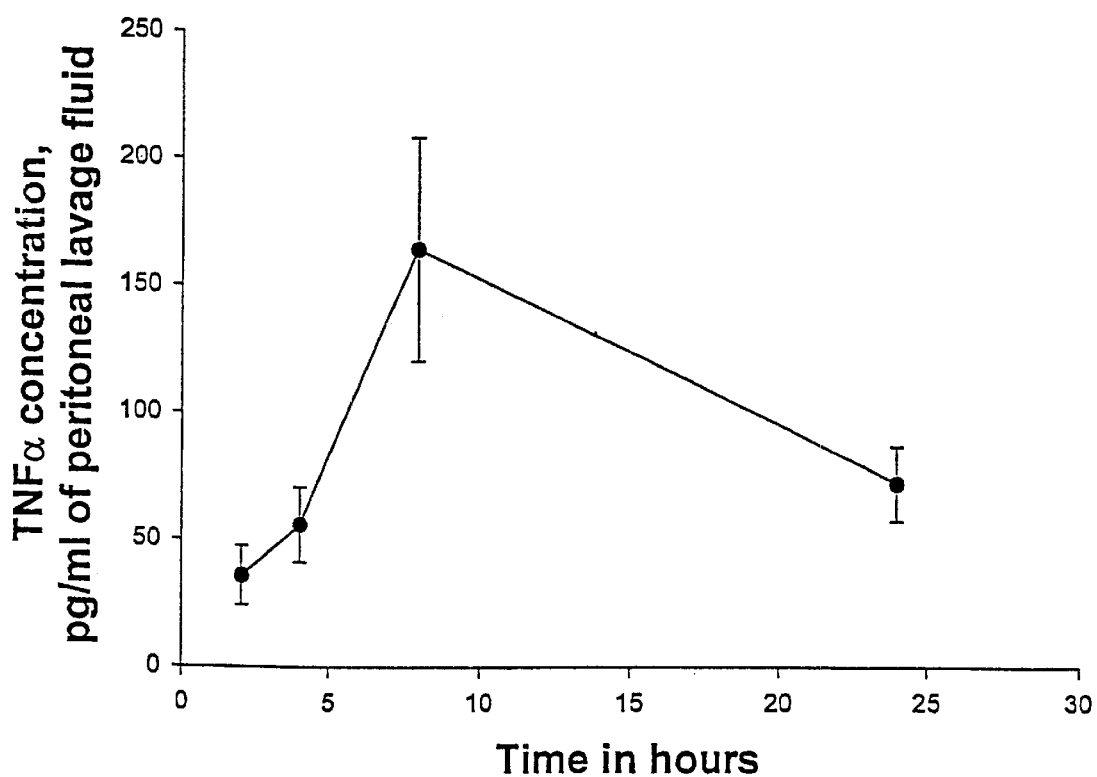
FIG. 6 is a graph showing the concentration of TNF-$\alpha$ (pg/ml) for mice injected intraperitoneally with bioactive glass and LPS, as described in Example 2.
Figure 7:
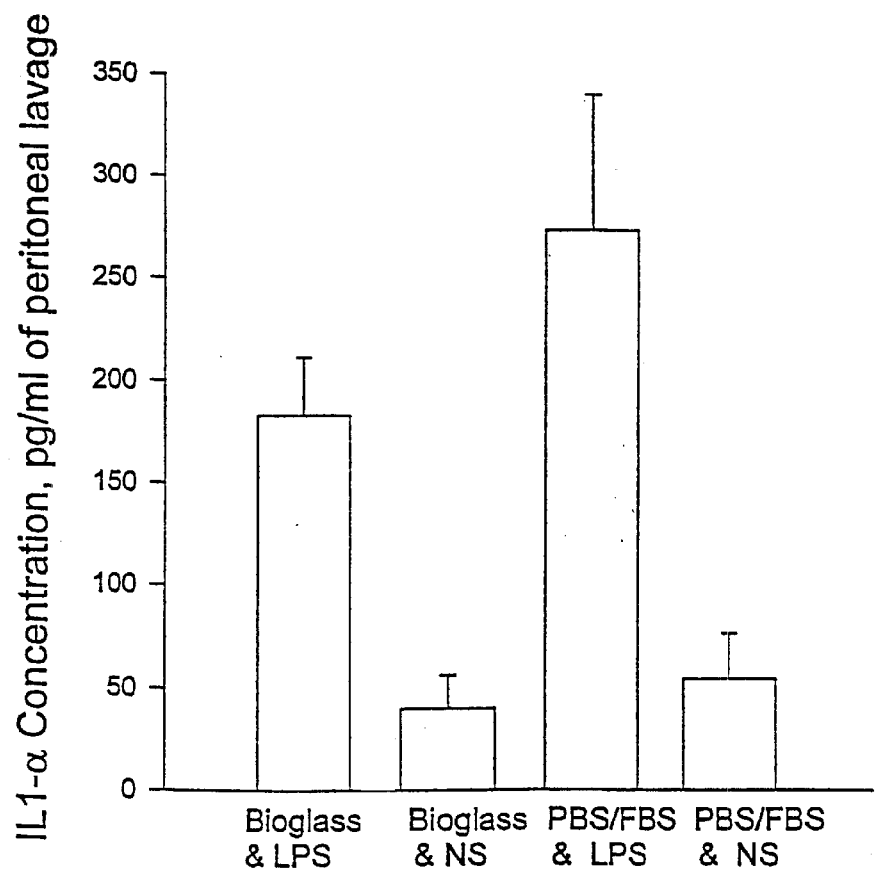
FIG. 7 is a graph showing the concentration of IL-1$\alpha$ (pg/ml) for mice injected intraperitoneally with bioactive glass and LPS, as described in Example 2.
Figure 8:
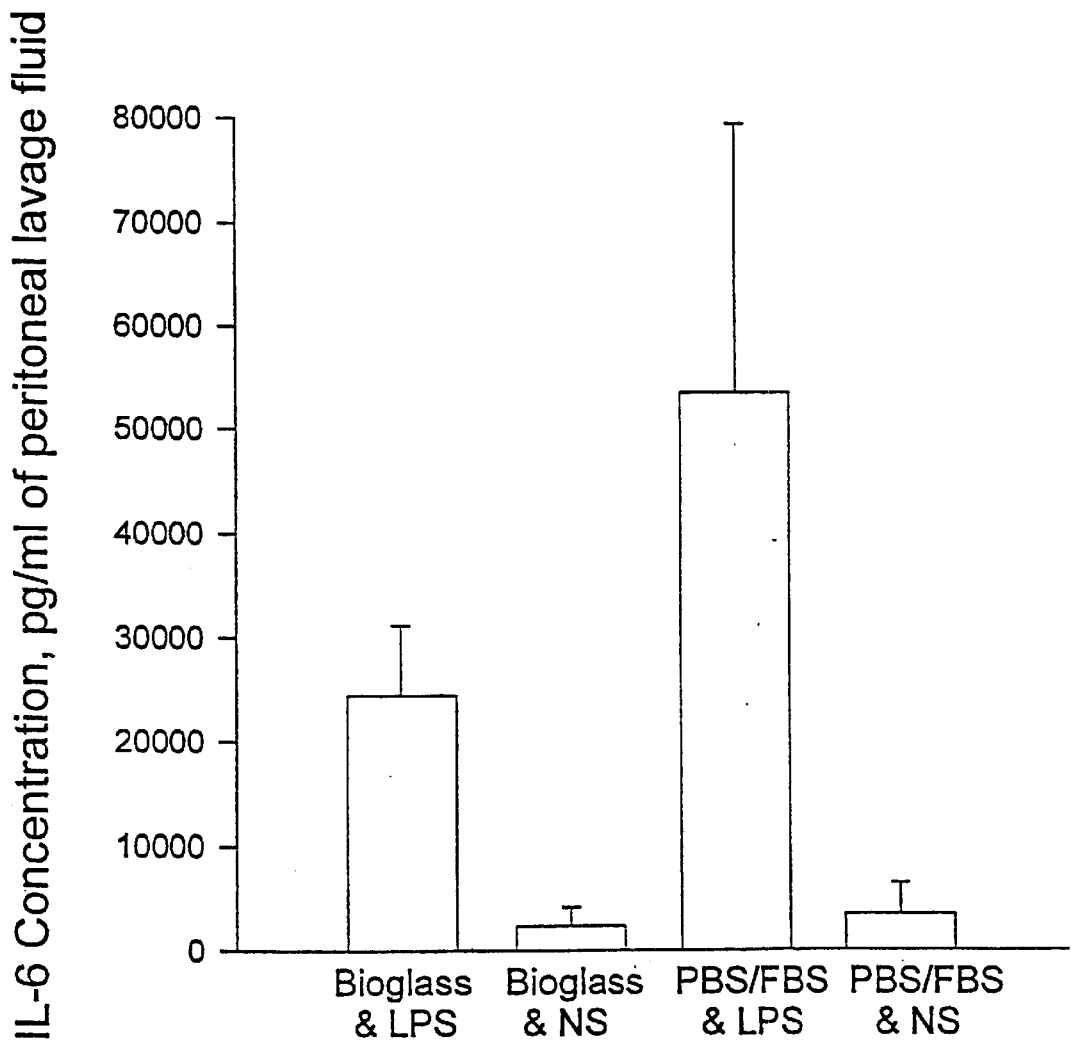
FIG. 8 is a graph showing the concentration of IL-6 (pg/ml) for mice injected intraperitoneally with bioactive glass and LPS, as described in Example 2.

Results: In the first study, all doses of bioactive glass were found to induce a significant IL-6 response (range 4,584–23, 112 pg/ml bioactive glass, 1,017±445 pg/ml±SEM buffer); however, the bioactive glass did not induce TNF-α or IL-1α production in the peritoneal lavage fluid. In the second study, mice that received bioactive glass particles prior to Dgal/LPS had significantly lower plasma TNF-α than did controls (bioactive glass: 13,047±4,126 pg/ml, control: 34,813±4,902 pg/ml, p<0.0038) (FIG. 5). Finally, peritoneal IL-6 and TNF-α were reduced in response to LPS by pretreatment with bioactive glass (IL-6 24,452±6,673 pg/ml and control: 53,330±2,586 pg/ml, bioactive glass: TNF-α—26±5 pg/ml and control: 91±49 pg/ml) (FIGS. 6–8).

Conclusion: Bioactive glass particles are a bioactive substance that when administered alone appear to elicit a significant initial IL-6 response without concurrent expression of TNF-α or IL-1α.

We claim:

1. A method for minimizing the production of TNF-α caused by an inflammatory response in a patient comprising administering locally a locally effective TNF-α lowering amount of bioactive glass particles with a size less than about 20 μm to the patient.

2. The method of claim 1 wherein the locally effective TNF-α lowering amount of bioactive glass particles is administered by intraperitoneal injection.

3. The method of claim 2 wherein the locally effective TNF-α lowering amount of bioactive glass particles is administered prophylactically or therapeutically to prevent or treat peritoneal adhesions.

4. The method of claim 2 wherein the locally effective TNF-α lowering amount of bioactive glass particles is administered by intraperitoneal injection of a composition comprising the bioactive glass particles, a suitable carrier for intraperitoneal injection, and one or more therapeutic agents.

5. The method of claim 4 wherein the one or more therapeutic agents are selected from the group consisting of healing promotion agents, growth factors, anti-inflammatory agents, and anesthetics.

6. The method of claim 2 wherein the bioactive glass particles have a size less than about 2 microns.

7. The method of claim 1 wherein the locally effective TNF-α lowering amount of bioactive glass particles is administered by inhalation.

8. The method of claim 1 wherein the locally effective TNF-α lowering amount of bioactive glass particles is administered by subcutaneous injection.

9. The method of claim 8 wherein the locally effective TNF-α lowering amount of bioactive glass particles is mixed with a biocompatible hydrogel.

10. The method of claim 8 wherein the locally effective TNF-α lowering amount of bioactive glass particles is administered at a site at which surgery is to be performed.

11. The method of claim 10 wherein the locally effective TNF-α lowering amount of bioactive glass particles is mixed with an anesthetic.

* * * * *